United States Patent

Wilson et al.

[11] Patent Number: 6,124,507
[45] Date of Patent: *Sep. 26, 2000

[54] ELECTRON DONORS

[75] Inventors: Stanley Edward Wilson; Robert Converse Brady, III, both of Houston, Tex.

[73] Assignee: Union Carbide Chemicals & Plastics Technology Corporation, Danbury, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/988,227

[22] Filed: Dec. 10, 1997

[51] Int. Cl.$^7$ .................................................. C07C 43/263
[52] U.S. Cl. .................... 568/648; 568/630; 568/656; 568/657; 502/126; 526/125
[58] Field of Search ..................... 568/628, 630, 568/631, 632, 634, 656, 657, 658, 648, 649, 655; 502/118, 125, 126; 526/125, 126, 127, 142, 144, 351

[56] References Cited

U.S. PATENT DOCUMENTS

| | | | |
|---|---|---|---|
| 3,764,629 | 10/1973 | Gurien et al. | 260/621 |
| 4,107,413 | 8/1978 | Giannini et al. | 526/114 |
| 4,107,414 | 8/1978 | Giannini et al. | 526/114 |
| 4,393,182 | 7/1983 | Goodall et al. | 526/125 |
| 4,680,054 | 7/1987 | Takematsu et al. | 71/93 |
| 4,710,482 | 12/1987 | Job | 502/127 |
| 4,971,936 | 11/1990 | Wilson et al. | 502/124 |
| 4,988,730 | 1/1991 | Korbonits et al. | 514/466 |
| 5,077,357 | 12/1991 | Job | 526/119 |
| 5,352,570 | 10/1994 | Begley | 430/544 |

FOREIGN PATENT DOCUMENTS

| | | |
|---|---|---|
| 831230A | 9/1993 | Belgium . |
| 98309523 | of 0000 | European Pat. Off. . |
| 0134576A2 | 3/1985 | European Pat. Off. . |
| 3427867 | 9/1993 | Germany . |
| 3633131 | 9/1993 | Germany . |
| 4048638 | 8/1993 | Japan . |
| 1297408 | 9/1993 | Japan . |
| 23278B4 | 3/1994 | Japan . |
| 2613169 | 2/1997 | Japan . |
| 898045 | 6/1962 | United Kingdom . |
| 9731954 | 9/1997 | WIPO . |

OTHER PUBLICATIONS

Article—Profft et al., "Aldehyde des Isohomobrenzkatechns (=3–Methylbrenzkatechin)", Journal fur praktische Chemie., 4. Eihe. Band 11. 1960, pp 309–326.
CA 94291–49–3, Sep. 16, 1985.

Primary Examiner—Johann Richter
Assistant Examiner—Sreeni Padmanabhan
Attorney, Agent, or Firm—P. A. Doody

[57] ABSTRACT

Novel compositions of the structure

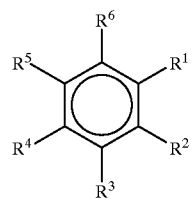

(I)

wherein $R^1$ and $R^2$ are each an alkoxy group which may be the same or different and have from one to ten carbon atoms, and $R^3$–$R^6$ are each individually, hydrogen, hydrocarbyl, hydrocarboxy, nitro, a silyl group or a halogen, with the provisos that if either $R^1$ or $R^2$ are methoxy, then at least one of $R^3$–$R^6$ is not hydrogen, if $R^1$ and $R^2$ are both ethoxy, then at least one of $R^3$–$R^6$ is not hydrogen, and $R^1$ and $R^2$ cannot both be methoxy, are taught herein, which may be used as electron donors, either internal or external, for catalysts used in the polymerization of olefins.

13 Claims, 2 Drawing Sheets

ELECTRON DONORS

BACKGROUND OF THE INVENTION

Ziegler-Natta catalysts are used to polymerize olefins. These catalysts contain a procatalyst made from an internal electron donor, a titanium source, a magnesium source and a halogenating agent (which may be combined with one of the other components). The use of these catalysts is known where this procatalyst is combined with an external electron donor or more commonly called a selectivity control agent ("SCA") and a cocatalyst. See, e.g., U.S. Pat. No. 5,093,415 to Brady et al.

One class of electron donors taught by the art is veratrole (1,2-dimethoxybenzene) and certain derivatives thereof which incorporate additional substituents on the benzene ring. U.S. Pat. No. 4,971,936 to Wilson et al. See also U.S. Pat. No. 4,107,413 to Giannini et al. However, these specific compounds have certain deficiencies in that catalysts made with them have low catalytic activity (<20 kg polymer/ procatalyst per hour) and produce polymers of low crystallinity (e.g., isotactic polypropylene with a xylene soluble of greater than 30% wt and a $L_{(iso)}$ (NMR) of less than 50 even with a SCA). The use of these electron donor compounds solely to produce polymers of low crystallinity is confirmed in Japanese patent application Nos. 2613169 and H1-307519. It is desirable to find electron donors which result in catalysts of improved activity and selectivity.

SUMMARY OF INVENTION

The novel electron donors (hereinafter "ED") of the present invention are of the formula

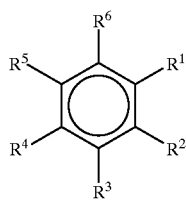

(I)

wherein $R^1$ and $R^2$ are each an alkoxy group, which may be the same or different, and have from one to ten carbon atoms, and $R^3$–$R^6$ are each individually, hydrogen, a hydrocarbyl group, a hydrocarboxyl group, a silyl group, a nitro group, or a halogen, with the provisos that (1) if either $R^1$ or $R^2$ are methoxy, then at least one of $R^3$–$R^6$ is not hydrogen, (2) if $R^1$ and $R^2$ are both ethoxy, then at least one of $R^3$–$R^6$ is not hydrogen, and (3) $R^1$ and $R^2$ cannot both be methoxy. These EDs are used in the manufacture of olefin polymerization catalysts with procatalysts having magnesium, titanium and halide as essential components.

DETAILED DESCRIPTION OF THE INVENTION

Figure 1:
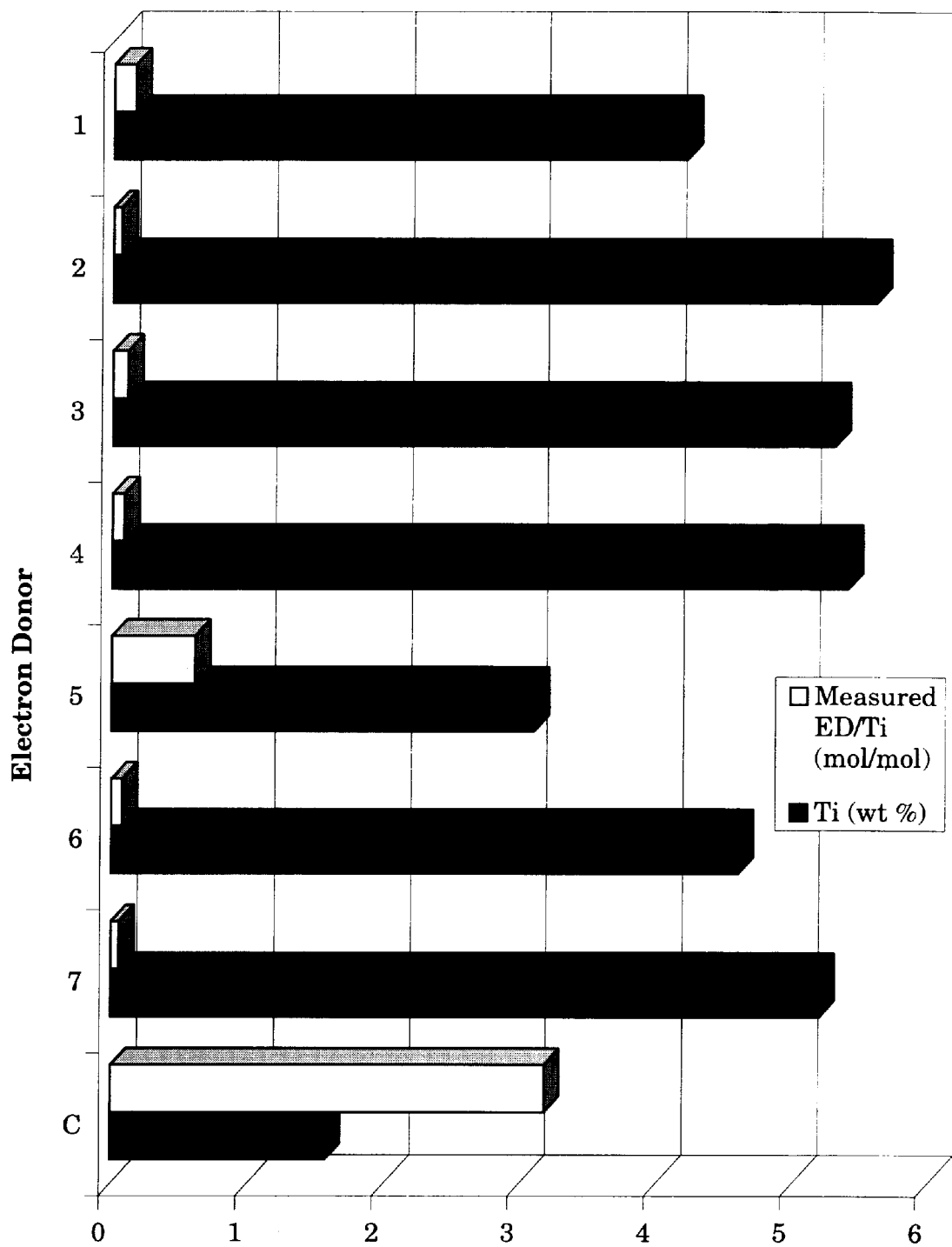
FIG. 1 is a plot of the content of various electron donor containing procatalysts (1–7 and C).

The electron donor of the present invention is of the Formula I above wherein $R^1$ and $R^2$ are alkoxy groups of $C_1$–$C_{10}$, which may be linear, branched or cyclic, $R^3$–$R^6$ are hydrogen, hydrocarbyl, hydrocarboxyl, nitro group, silyl or a halogen, with the provisos that (1) if either $R^1$ or $R^2$ are methoxy, then at least one of $R^3$–$R^6$ is not hydrogen; (2) if $R^1$ and $R^2$ are both ethoxy, then at least one of $R^3$–$R^6$ is not hydrogen; and (3) $R^1$ and $R^2$ cannot both be methoxy.

$R^1$ and $R^2$ may the same or different from each other with the above provisos. Preferably $R^1$ and $R^2$ are alkoxy groups of $C_2$–$C_{10}$, more preferably $C_2$–$C_6$. $R^1$ and $R^2$ may be branched; however, when the branching of the alkoxy functionalities ($R^1$, $R^2$) is at the carbon attached to the oxygen atom, the donor does not attach to the catalyst well, so it is preferred to have the steric bulk created by branching away at least one carbon away from the oxygen atom (e.g., isopentoxy). Specific alkoxy groups for $R^1$ and $R^2$ are propoxy, n-butoxy, pentoxy, isopentoxy, hexoxy, n-octoxy, 3-cyclohexylpropoxy and 4-cyclopentylbutoxy. Preferably, at least one alkoxy group is an ethoxy wherein the other alkoxy group may be the same or an alkoxy of $C_3$–$C_6$.

The $R^3$–$R^6$ groups each individually may be hydrogen, hydrocarbyl, (e.g., an alkyl (e.g., methyl or t-butyl), cycloaliphatic (e.g, cyclopentyl), aryl (e.g., napththyl or alkaryl), hydrocarboxy (e.g., an alkoxy, aryloxy or aralkoxy), silyl (e.g., silyl or trimethyl silyl), nitro, or a halogen (e.g., Cl or F). If $R^3$–$R^6$ are hydrocarbyl or hydrocarboxy, preferably it has from one to ten carbon atoms. Preferably, only one or none of $R^3$ to $R^6$ are groups other than hydrogen. If one of $R^1$ and $R^2$ is methoxy, at least one of $R^3$–$R^6$ is not hydrogen. Preferably any substitution is at the $R^4$ position.

Some specific EDs are 1-ethoxy-2-methoxy-3-methylbenzene; 1,2-diethoxy-3-fluorobenzene; 1,2-diethoxy-3-methylbenzene; 1,2-diethoxy-4-t-butylbenzene; 1,2-diethoxy-3-trimethylsilylbenzene; 1-ethoxy-2-propoxybenzene, 1,2-di-propoxybenzene; 1,2-dibutoxybenzene; 1,2-diethoxynaphthalene; 2,3-diethoxy-5,6,7,8-tetrahydronaphthalene and 1-ethoxy-2-n-hexoxybenzene. The preferable ED is 1-ethoxy-2-isopentoxybenzene.

A. Electron Donor Manufacture

The ED may be manufactured using 2-alkoxy phenol (e.g., 2-ethoxy phenol), which is commercially available, as a starting material. This is combined with an alkyl halide of the desired alkoxy substituent, e.g., ethyl iodide in the presence of a base. Such substitution by salt elimination reactions are known in the art. The benzene ring may be substituted at the 3–6 positions using the alcohol of the substituent in an acid catalyzed reaction in solvent at elevated temperature. In the case of a halogenated benzene, it is preferred to start with commercially available halogenated catechol and prepare alkoxy compounds as described above.

The solvent for this reaction is preferably water. Separation from water may be by phase separation techniques known in the art, e.g., solvent extraction.

These EDs may be used either as the internal ED, the SCA or as both.

B. Procatalyst

The procatalysts contain magnesium, titanium and a halogen, along with either the above-recited ED or an ED known in the art, said procatalyst being used to form a catalyst for the polymerization of olefins. The halide is introduced into the procatalyst with either the magnesium or titanium source.

i. Magnesium

The magnesium source may be a magnesium halide, alkyl, aryl, alkaryl, alkoxide, alkaryloxide or aryloxide, alcohol adducts thereof or carbonated derivatives thereof, but preferably is a carbonated magnesium dialkoxide or a carbonated magnesium diaryloxide. Magnesium compounds containing one alkoxide and one aryloxide group can also be employed, as well as magnesium compounds containing a halogen in addition to one alkoxide, alkaryloxide or aryloxide group. The alkoxide groups, when present, most suitably contain from 1 to 8 carbon atoms, preferably from 2 to 6 carbon atoms. The aryloxide groups when present, most suitably contain from 6 to 10 carbon atoms. When halogen is present, it is preferably chlorine.

Among the magnesium dialkoxides and diaryloxides which can be employed are those of the formula $Mg(O(C(O)OR')_x(OR'')_{2-x}$, wherein R' and R'' are alkyl, alkaryl or aryl groups, and x is about 0.1 to about 2. The most preferable magnesium compound is carbonated magnesium diethoxide (CMEO),

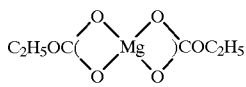

Optionally, the magnesium may be halogenated with an additional halogenating agent, e.g., thionyl chloride or alkylchlorosilanes, prior to its contact with the tetravalent titanium source.

A somewhat different type of magnesium source is described by the general formula $$Mg_4(OR^3)_6(R^4OH)_{10}A \qquad (I)$$

in which each $R^3$ or $R^4$ is a lower alkyl of up to 4 carbon atoms inclusive and A is one or more anions having a total charge of −2. The manufacture of this magnesium source is disclosed in U.S. Pat. No. 4,710,482 to Job which is incorporated herein by reference.

Another magnesium source is one that contains moieties of magnesium and titanium and probably moieties of at least some of halide, alkoxide and a phenolic compound. Such complex procatalyst precursors are produced by contacting a magnesium alkoxide, a titanium alkoxide, a titanium halide, a phenolic compound and an alkanol. See U.S. Pat. No. 5,077,357 to Job, which is incorporated herein by reference.

ii. Titanium

The titanium source for the procatalyst is a tetravalent titanium which contains at least two halogen atoms, and preferably contains four halogen atoms, e.g., $Ti(OR^5)_nX_{4-n}$, wherein $R^5$ is a hydrocarbon, and X is a halide and n is 0 to 2. Most preferably these halogen atoms are chlorine atoms. Titanium compounds containing up to two alkoxy, alkaryloxy or aryloxy groups can be employed. The alkoxy groups, when present, most suitably contain from 1 to 8 carbon atoms, preferably 2 to 6 carbon atoms. The aryloxy or alkaryloxy groups, when present, most suitably contain from 6 to 12 carbon atoms, preferably from 6 to 10 carbon atoms. Examples of suitable alkoxy- and aryloxy-titanium halides include diethoxy titanium dibromide, isopropoxy titanium triiodide, dihexoxy titanium dichloride, and phenoxy titanium trichloride. The most preferable titanium source is $TiCl_4$.

iii. Standard EDs

If the ED of the present invention is used as an SCA, other EDs may be used as the internal ED, which may be those EDs free from active hydrogens which are conventionally employed in the formation of titanium-based procatalysts. Such EDs include ethers, esters, amines, imines, nitriles, phosphines, stibines, and arsines. The preferred EDs are esters, particularly alkyl esters of aromatic monocarboxylic or dicarboxylic acids. Examples of such EDs are methyl benzoate, ethyl benzoate, ethyl p-ethoxybenzoate, ethyl p-ethylbenzoate, diethyl phthalate, dimethyl naphthalene dicarboxylate, diisobutyl phthalate (DIBP) and diisopropyl tetrephthalate. The ED is a single compound or is a mixture of compounds but preferably the ED is a single compound. Of the preferred ester EDs, ethyl benzoate (EB) and DIBP are particularly preferred if a standard ED is used.

iv. Procatalyst Manufacture

The magnesium compound is reacted (i.e., halogenated) with the tetravalent titanium halide in the presence of an ED and preferably a halohydrocarbon. Optionally, an inert hydrocarbon diluent or solvent also may be present.

The halohydrocarbon employed may be aromatic, aliphatic, or alicyclic. Most preferably, the halogen of the halohydrocarbon is chlorine. Aromatic halohydrocarbons are preferred, particularly those containing from 6 to 12 carbon atoms, preferably 6 to 10 carbon atoms. Preferably such halohydrocarbons contain 1 or 2 halogen atoms, although more may be present if desired. Suitable aromatic halohydrocarbons include, but are not limited to chlorobenzene, bromobenzene, dichlorobenzene, dichlorodibromobenzene, chlorotoluene, dichlorotoluene, and chloronaphthalene. The aliphatic halohydrocarbons contain from 1 to 12 carbon atoms, preferably from 1 to 9 carbon atoms and at least 2 halogen atoms. Suitable aliphatic halohydrocarbons include, but are not limited to dibromomethane, trichloromethane, 1,2-dichloroethane, trichloroethane, dichlorofluoroethane, hexachloroethane, trichloropropane, chlorobutane, dichlorobutane, chloropentane, trichlorofluorooctane, tetrachloroisooctane, dibromodifluorodecane, carbon tetrachloride, and trichloroethane. The alicyclic halohydrocarbons which can be employed contain from 3 to 12 carbon atoms, and preferably from 3 to 9 carbon atoms, and at least 2 halogen atoms. Suitable alicyclic halohydrocarbons include dibromocyclobutane, and trichlorocyclohexane.

The optional inert hydrocarbon diluent may be aliphatic, aromatic or alicyclic. Some exemplary diluents are isopentane, n-octane, isooctane, xylene, or toluene.

Halogenation of the magnesium compound with the halogenated tetravalent titanium halide is effected employing an excess of the titanium halide. At least 2 moles of the titanium halide should be employed per mole of the magnesium compound. Preferably from about 4 moles to about 100 moles of the titanium halide are employed per mole of the magnesium compound, and most preferably from about 4 moles to about 20 moles of the titanium halide are employed per mole of the magnesium compound.

The halohydrocarbon is employed in an amount sufficient to dissolve the titanium halide and the ED, and to adequately disperse the magnesium compound. Usually the dispersion contains from about 0.005 to about 2.0 moles of the solid magnesium compound per mole of halohydrocarbon, preferably from about 0.01 to about 1.0 mole of the solid magnesium compound per mole of the halohydrocarbon. The ED is employed in an amount sufficient to provide a molar ratio of said compound to the titanium halide of from about 0.0005:1 to about 2.0:1, preferably from about 0.001:1 to about 0.1:1. 1:100 to 100:1 by volume of halohydrocarbon to diluent may be used.

Halogenation can be effected at a temperature of from about 60° C. to about 150° C., preferably from about 90° C. to about 140° C. Generally, as the temperature is increased the ED content drops while the titanium loading rises. Usually the reaction is allowed to proceed over a period of 0.1 to 6 hours, preferably between about 0.5 to about 3.5 hours. For convenience, halogenation is usually effected at atmospheric pressure, although a range of pressures can be employed, e.g, 0.5 atm (50,700 Pa) to 5 atm (507,000 Pa). The halogenated product, like the starting magnesium compound, is a solid material which can be isolated from the liquid reaction medium by drying, filtration, decantation, evaporation, distillation or any suitable method.

After separation, the halogenated product may be treated one or more times with additional tetravalent titanium halide to remove residual alkoxy and/or aryloxy groups and maximize catalyst activity or other desired properties. Preferably, the halogenated product is treated at least twice with separate portions of the tetravalent titanium halide. Generally, the reaction conditions employed to treat the halogenated product with the titanium halide are the same as those employed during the initial halogenation of the magnesium compound, and the ED may or may not be present during this treatment, though it is preferred that it be present. The halohydrocarbon usually is employed to dissolve the titanium halide and disperse the solid, halogenated product. If desired, the halogenated product may be treated with the acid halide before or after it is treated with the titanium compound for the second time. From 5 mmol to 200 mmol of the acid halide generally are employed per gram atom of magnesium of the halogenated product. Suitable acid halides include benzoyl chloride, phthaloyl dichloride, 2,3-naphthalenedicarboxylic acid dichloride, endo-5-norbornene-2,3-dicarboxylic acid dichloride, maleic acid dichloride, citraconic acid dichloride, and the like.

After the solid halogenated product has been treated one or more times with additional tetravalent titanium halide, it is separated from the liquid reaction medium, washed with an inert hydrocarbon to remove unreacted titanium compounds, and dried. Drying may be by filtration, evaporation, heating or other methods known in the art.

The final washed procatalyst product suitably has a titanium content of from about 0.5 percent by weight to about 6.0 percent by weight, preferably from about 1.5 percent by weight to about 4.0 percent by weight. The atomic ratio of titanium to magnesium in the final procatalyst product is suitably between about 0.01:1 and about 0.2:1, preferably between about 0.02:1 and about 0.1:1. The ED is present in the procatalyst in a ratio of ED to magnesium of from about 0.001:1 to about 10.0:1, preferably from about 0.02:1 to about 2.0:1.

C. Catalyst

The olefin polymerization catalyst includes the above-described procatalyst, a cocatalyst and a selectivity control agent ("SCA").

i. Cocatalyst

The cocatalyst may be chosen from any of the known activators of olefin polymerization catalyst systems, but organoaluminum compounds are preferred. Such cocatalysts can be employed individually or in combinations thereof. Suitable organoaluminum cocatalysts have the formula $Al(R''')_d X_e H_f$ wherein: X is F, Cl, Br, I or OR'''', R''' are saturated hydrocarbon radicals containing from 1 to 14 carbon atoms, which radicals may be the same or different, and, if desired, substituted with any substituent which is inert under the reaction conditions employed during polymerization, d is 1 to 3, e is 0 to 2, f is 0 or 1, and d+e+f=3. Trialkylaluminum compounds are particularly preferred, particularly those wherein each of the alkyl groups contains from 1 to 6 carbon atoms, e.g., $Al(CH_3)_3$, $Al(C_2H_5)_3$, $Al(i-C_4H_9)_3$, and $Al(C_6H_{13})_3$.

ii. SCA

The SCA is either the ED of Structure I or one of those known in the art. The SCA is the electron donor of Structure I, if the ED is not of Structure I. The SCAs known in the art include, but are not limited to, silicon compounds, esters of carboxylic acids, (especially diesters), monoethers, diethers (e.g., 1,3 dimethoxy propane or 2,2 diisobutyl-1,3 dimethoxy propane), and amines (e.g., tetramethyl piperdine).

Preferably, the silicon compounds employed as SCAs contain at least one silicon-oxygen-carbon linkage. Suitable silicon compounds include those having the formula $R^1_m SiA_n X_p$ wherein: $R^1$ is a hydrocarbon radical containing from 1 to 20 carbon atoms, Y is $—OR^2$ or $—OCOR^2$ wherein $R^2$ is a hydrocarbon radical containing from 1 to 20 carbon atoms, X is hydrogen or halogen, m is an integer having a value of from 0 to 3, n is an integer having a value of from 1 to 4, p is an integer having a value of from 0 to 1, and preferably 0, and m+n+p=4. Preferably, $R^1$ and $R^2$ are alkyl, aryl or alkaryl ligands of $C_1-C_{10}$. Each $R^1$ and $R^2$ may be the same or different, and, if desired, substituted with any substituent which is inert under the reaction conditions employed during polymerization. Preferably, $R^2$ contains from 1 to 10 carbon atoms when it is aliphatic and may be sterically hindered or cycloaliphatic, and from 6 to 10 carbon atoms when it is aromatic.

Examples of $R^1$ include cyclopentyl, t-butyl, isopropyl, cyclohexyl or methyl cyclohexyl. Examples of $R^2$ include methyl, ethyl, butyl, isopropyl, phenyl, benzyl and t-butyl. Examples of X are Cl and H. Preferred silicon SCAs are alkylalkoxysilanes such as diethyldiethoxysilane, diphenyl dimethoxy silane, diisobutyldimethoxysilane, cyclohexylmethyldimethoxysilane, n-propyltrimethoxysilane or dicyclopentyl dimethoxysilane.

Silicon compounds in which two or more silicon atoms are linked to each other by an oxygen atom, i.e., siloxanes or polysiloxanes, may also be employed, provided the requisite silicon-oxygen-carbon linkage is also present. Other preferred SCAs are esters of aromatic monocarboxylic or dicarboxylic acids, particularly alkyl esters, such as PEEB, DIBP, and methyl paratoluate.

In one modification, the SCA is a portion of the ED added during the procatalyst production if multiple electron donors are used or both SCA and ED may be of Structure I. In an alternate modification the SCA is provided at the time of the contacting of procatalyst and cocatalyst.

The SCA is provided in a quantity sufficient to provide from about 0.01 mole to about 100 moles per mole of titanium in the procatalyst. It is preferred that the SCA is provided in a quantity sufficient to provide from about 0.5 mole to about 70 moles per mole of titanium in the procatalyst, with about 8 moles to about 50 moles being more preferred. Mixtures of two or more SCA's may be used.

The components of the olefin polymerization catalyst can be contacted by mixing in a suitable reactor outside the system in which olefin is to be polymerized and the catalyst thereby produced subsequently is introduced into the polymerization reactor. The premixed components may be dried after contact or left in the contact solvent. Alternatively, however, the catalyst components may be introduced separately into the polymerization reactor. As another alternative, two of the components may be mixed partially or completely with each other (e.g. premixing SCA and cocatalyst) prior to being introduced into the polymerization reactor. Another alternative is to contact the procatalyst with an aluminum alkyl halide prior to reaction with the other catalyst components. A different alternative is to pre-polymerize a small amount of olefin with the catalyst components or put any of the components on a support, e.g., silica or a non-reactive polymer.

The catalyst should have an activity of at least about 25 kg polymer per gram procatalyst per hour, preferably at least about 35 kg polymer per gram procatalyst per hour.

D. Polymerization

The olefin polymerization catalyst is useful in the polymerization of olefins of up to 20 carbon atoms, inclusive, e.g., ethylene, propylene, 1-butene, 1-dodecene, 1,3-butadiene, 7-methyl-1,6-octadiene, or mixtures thereof, are contemplated herein as well. It is preferred that alpha-olefins of 3 carbon atoms to 10 carbon atoms, such as propylene, butene-1 and pentene-1 and hexene-1, are homopolymerized, though copolymers, such as $C_2/C_3$ and $C_3/C_4$ copolymers, and terpolymers may also be produced. Moreover, multi-stage polymers may be produced with the catalyst of the present invention, e.g., a propylene homopolymer with an ethylene-propylene rubber.

The invention is useful for the production of isotactic, crystalline polypropylene (iPP) and other stereospecific polymerizations. Preferably, the xylene solubles (XS) of iPP as measured according to 21 CFR 177.1520 are less than fifteen (15) percent by weight, more preferably, less than eight (8) weight percent of the polymer and even more preferably less than five weight percent of the polymer.

Moreover, for iPP the $L_{(iso)}$ as measured by NMR is greater than 30, more preferably greater than 50, most preferably greater than 70.

The polymerization is conducted under polymerization conditions in a liquid phase, slurry phase or a gas-phase process employing a stirred or fluidized bed. In both the liquid phase and the gas-phase polymerization processes, molecular hydrogen is added to the reaction mixture as a chain transfer agent to regulate the molecular weight of the polymeric product.

EXAMPLES

The following abbreviations are used in the examples.

| Abbreviation | Meaning |
| --- | --- |
| MT | A magnesium source produced as described in U.S. Pat. No. 5,077,357 |
| DCPDMS | dicyclopentyldimethoxysilane (SCA) |
| TEAL | triethylaluminum (cocatalyst) |
| MCB | monochlorobenzene |
| XS | xylene solubles (wt %) (21 CFR 177.1520) |

ED Synthesis

This synthesis of 1-ethoxy-2-isopentoxybenzene is representative of the synthesis of the non-commercially available EDs via substitution reactions by salt elimination. 200 mmol of 2-ethoxyphenol was added to a stirring solution of 417 mmol of sodium hydroxide in 90 ml of water. Following the addition of 400 mmol of 1-bromo-3-methylbutane, the mixture was refluxed for 6 hours. The two phase liquid was extracted with hexanes. The organic phase was washed with a sodium hydroxide solution followed by a sodium chloride solution. The organic phase was then dried over magnesium sulfate and distilled. A 38% yield was obtained of the 1-ethoxy-2-isopentoxybenzene product as determined by $^1$H NMR.

Procatalyst Preparation 3.0 g of MT containing 12% Mg was slurried in a volume of 60 ml of a 50/50 by (vol/vol) mixture of $TiCl_4$/MCB with an ED for 60 minutes at a temperature ranging from 110 to 130° C. The resulting mixture was filtered while hot. The recovered solids were slurried in 60 ml of the fresh 50/50 mixture and ED for 60 minutes at the same temperature used in the first step. The resulting mixture was filtered while hot. The recovered solids were slurried again in 60 ml of the fresh 50/50 mixture and ED for 60 minutes at the same temperature used in the first step. The resulting mixture was filtered while hot and the solids recovered. The solids were rinsed three times with 70 ml of isooctane at room temperature, and then dried for at least two hours under flowing nitrogen. Typical recovery of the precursor was approximately 2 g. The volume of ED added to each step, the temperature, and analysis of these procatalyst preparations are shown in Table 1. A comparative example (C) of a precursor made with veratrole as the internal ED had a lower Ti content and a higher ED/Ti ratio than the EDs of the present invention. FIG. 1 is a plot of the ED versus the procatalyst properties of ED/Ti mole ratio and Ti weight percent.

Figure 2:
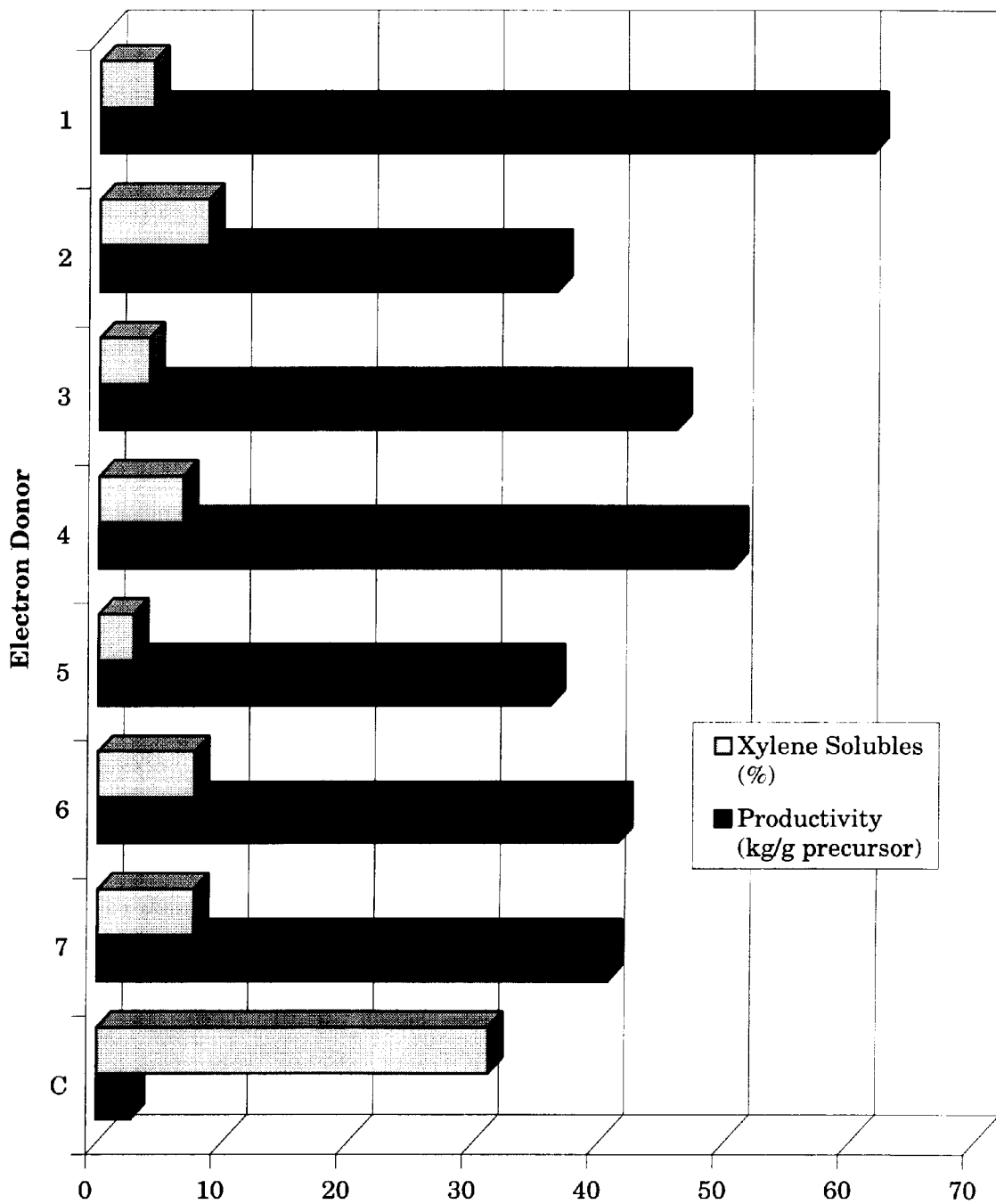
FIG. 2 is a plot of catalyst productivity and for catalysts containing certain electron donors (1–7 and C) and xylene solubles for polymers produced from said catalysts.

Liquid Propylene Stirred Polymerization Procedure 2.7 l of liquid propylene was added to a cooled 1-gallon autoclave that had been dried under a stream of nitrogen at greater than 90° C. To the stirred autoclave at 62° C. were added 1.5 l of hydrogen, 58 µl of DCPDMS (0.24 mmol), 3.6 ml of 5.0% by weight TEAL solution in heptane (1.0mmol), and 7.5 mg of procatalyst as a 5% by weight mineral oil slurry. The polymerization took place for 60 minutes at 67° C. The results of these polymerizations are shown in the Table wherein "Productivity" refers to the yield of polypropylene polymer in kg of polymer/g procatalyst per hour. A comparative example (C) of polymerization with a catalyst made with veratrole as the internal ED had a lower productivity and higher XS than catalysts made with EDs of the present invention. FIG. 2 is a plot of ED versus the catalyst productivity and XS of polymer produced by the catalyst.

TABLE I

| Example | Electron Donor | ED (ml) | Prep Temp (° C.) | Ti (wt %) | Measured ED/Ti (mol/mol) | Productivity (kg/g precursor) | Xylene Solubles (%) |
|---|---|---|---|---|---|---|---|
| 1 | 1-Ethoxy-2-isopentoxybenzene | 1.4 | 130 | 4.2 | 0.16 | 61.6 | 4.3 |
| 2 | 1,2-Diethoxy-3-methylbenzene | 1.5 | 110 | 5.6 | 0.06 | 36.4 | 8.7 |
| 3 | 1,2-Diethoxy-3-fluorobenzene | 1.2 | 130 | 5.3 | 0.11 | 46.0 | 4.0 |
| 4 | 1,2-Diethoxy-3-(trimethylsilyl)benzene | 0.7 | 130 | 5.4 | 0.09 | 50.6 | 6.7 |
| 5 | 1,2-Diethoxy-4-t-butylbenzene | 1.5 | 130 | 3.1 | 0.61 | 36.0 | 2.8 |
| 6 | 1,2-Di-n-propoxybenzene | 1.2 | 130 | 4.6 | 0.08 | 41.4 | 7.7 |
| 7 | 1,2-Di-n-butoxybenzene | 1.6 | 130 | 5.2 | 0.06 | 40.7 | 7.7 |
| C | Veratrole | 1.0 | 130 | 1.6 | 3.18 | 2.7 | 31.2 |

We claim:

1. A compound of the structure

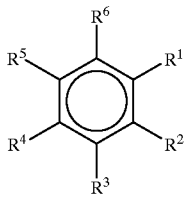

(I)

wherein $R^1$ is ethoxy, and $R^2$ is an alkoxy group having from one to ten carbon atoms, $R^3$ is hydrogen, and $R^4$–$R^6$ are each individually, hydrogen, a hydrocarbyl group, a hydrocarboxyl group, a nitro group, a silyl group or a halogen, with the provisos that (1) if $R^2$ methoxy, then at least one of $R^4$–$R^6$ is not hydrogen, and (2) if $R^1$ and $R^2$ are both ethoxy, then at least one of $R^4$–$R^6$ is not hydrogen.

2. A compound according to claim 1, wherein $R^3$–$R^6$ are hydrogen.

3. A compound according to claim 2, wherein $R^2$ is isopentoxy.

4. A compound according to claim 1, wherein $R^2$ is selected from the group consisting of: propoxy, n-butoxy, pentoxy, isopentoxy, hexoxy, n-octoxy, 3-cyclohexyl propoxy and 4-cyclopentyl butoxy.

5. A compound according to claim 1, wherein at least one of $R^4$–$R^6$ is selected from the group consisting of: alkyl, silyl or halogen.

6. A compound according to claim 5, wherein $R^4$ is selected from the group consisting of alkyl, silyl or halogen and $R^3$, $R^5$ and $R^6$ are each hydrogen.

7. A process comprising reacting a. a magnesium compound; with b. a titanium compound;

wherein at least (a) or (b) is halogenated, in the presence of a compound according to claim 1.

8. A reaction product made according to the process of claim 7.

9. A composition comprising a compound according to claim 1, and additionally comprising a procatalyst having titanium, magnesium, halide and an internal electron donor.

10. A composition comprising a compound according to claim 1, and additionally comprising magnesium, titanium and halide.

11. A composition according to claim 10, wherein $R^1$ is ethoxy, and $R^2$ is isopentoxy.

12. A composition according to claim 11, wherein $R^3$–$R^6$ are hydrogen.

13. A composition according to claim 12, wherein the titanium, magnesium and halide are the reaction product of $TiCl_4$ and carbonated magnesium ethoxide.

* * * * *